United States Patent [19]

Kelly et al.

[11] Patent Number: 5,375,604
[45] Date of Patent: Dec. 27, 1994

[54] TRANSPORTABLE MODULAR PATIENT MONITOR

[75] Inventors: Clifford M. Kelly, Goffstown, N.H.;
Bengt Hermanrud, Topsfield, Mass.;
Wolfgang Scholz, Beverly, Mass.;
Thomas Bishop, Wenham, Mass.;
Michael Maschke, Beverly, Mass.

[73] Assignee: Siemens Medical Electronics, Inc., Danvers, Mass.

[21] Appl. No.: 988,989

[22] Filed: Dec. 11, 1992

[51] Int. Cl.$^5$ .......................................... A61B 5/0205
[52] U.S. Cl. .................................... 128/671; 128/670
[58] Field of Search ................................ 128/670–671, 128/687, 672, 736, 716, 633; 340/573

[56] References Cited

FOREIGN PATENT DOCUMENTS

| | | |
|---|---|---|
| 3,848,582 | 11/1974 | Milani et al. |
| 3,858,576 | 1/1975 | Dehnert et al. |
| 4,245,650 | 1/1981 | Welker et al. |
| 4,249,538 | 2/1981 | Musha et al. |
| 4,325,385 | 4/1982 | Holte |
| 4,356,475 | 10/1982 | Neumann et al. |
| 4,378,021 | 3/1983 | Strand |
| 4,407,295 | 10/1983 | Steuer et al. ................ 128/671 X |
| 4,577,639 | 3/1986 | Simon et al. |
| 4,606,352 | 8/1986 | Geddes et al. |
| 4,715,385 | 12/1987 | Cudahy et al. ................ 128/710 |
| 4,724,844 | 2/1988 | Rafelson |
| 4,779,199 | 10/1988 | Yoneda et al. |
| 4,814,759 | 3/1989 | Gombrich et al. |
| 4,895,161 | 1/1990 | Cudahy et al. |
| 4,909,260 | 3/1990 | Salem et al. ................ 128/671 X |
| 4,940,058 | 7/1990 | Taff et al. ................ 128/671 X |
| 4,966,154 | 10/1990 | Cooper et al. |
| 4,974,607 | 12/1990 | Miwa ................ 128/670 X |
| 4,982,738 | 1/1991 | Griebel ................ 128/671 X |
| 5,012,411 | 4/1991 | Policastro et al. |
| 5,024,225 | 6/1991 | Fang |
| 5,025,808 | 6/1991 | Hafner |
| 5,029,590 | 7/1991 | Allain et al. |
| 5,036,856 | 8/1991 | Thornton |
| 5,197,489 | 3/1993 | Conlan ................ 128/671 X |

FOREIGN PATENT DOCUMENTS 0346685  12/1989  European Pat. Off.

(List continued on next page.)

OTHER PUBLICATIONS

Hewlett–Packard Brochure: Patient Data Management System–System Description, Manual Part No. 78707-91998-9, Jan. 1982.

(List continued on next page.)

*Primary Examiner*—Angela D. Sykes
*Attorney, Agent, or Firm*—Lawrence C. Edelman

[57] ABSTRACT

Patient monitoring apparatus for use in an environment which includes a communications network and a plurality of sensors. The apparatus provides collection and display of patient data signals collected from a medical patient using the sensors. The apparatus comprises a portable monitor coupled to a plurality of data acquisition modules, which are in turn coupled to the sensors. The data acquisition modules include cartridges, which mount on the portable monitor, and independently positionable pods. The pods reduce the number of cables extending between the patient's bed and the portable monitor by combining signals from many sensors into a single output signal for transmission to the monitor. The modules collect patient data in analog form from the sensors and provide digital data signals to the monitor. The portable monitor includes: a display device for displaying the patient data, and storage for the patient data. The portable monitor is coupled to the docking station. The portable monitor receives power from the docking station, and transfers data to the network by way of the docking station. Patient data are displayed on either one of the portable monitor or a remote display device attached to the docking station. The portable monitor is rapidly detached from the docking station for transporting the patient.

26 Claims, 8 Drawing Sheets

FOREIGN PATENT DOCUMENTS

| | | |
|---|---|---|
| 0466272A1 | 7/1991 | European Pat. Off. . |
| 0488410 | 6/1992 | European Pat. Off. . |
| 2145020 | 2/1973 | France . |
| 7145754 | of 0000 | Germany . |
| 524992 | 8/1972 | Switzerland . |
| WO81/02832 | 10/1981 | WIPO . |
| 8900024 | 6/1987 | WIPO . |

OTHER PUBLICATIONS

Marquette Electronics, Inc. brochure: Unity Monitoring Network–The Power of Integrated Patient Monitoring, 1990.

Webster J., Encyclopedia of Medical Devices and Instrumentation, vol. 3, pp. 2016-2025, John Wiley & Sons, 1988.

Corometrics Medical Systems, Inc. brochure: "Neotrak 515A Neonatal Monitoring System", 1982.

G. Moore, The Hospital Connection, Computer Systems Europe, May, 1989.

Kuroiwa, T., The Application of the I.C. Card in the Area of Medical Health, Proceedings of the IEEE/Ninth Annual Conference of the Engineering in Medicine and Biology Society, Nov., 1987.

Shaffer, J. et al, Semi-Automated Heart Station, Proceedings of the 26th Annual Conference on Engineering in Medicine & Biology. p. 40, 1973.

Siemens Medical Systems, Inc. brochure "Sirecust 1280 & 1281", order No. A91004-M3330.K079-02.7600.

Siemens Medical Systems, Inc. brochure: System Sirecust LIM Cartridge, order No. A91004-M3331-G91-05-7600.

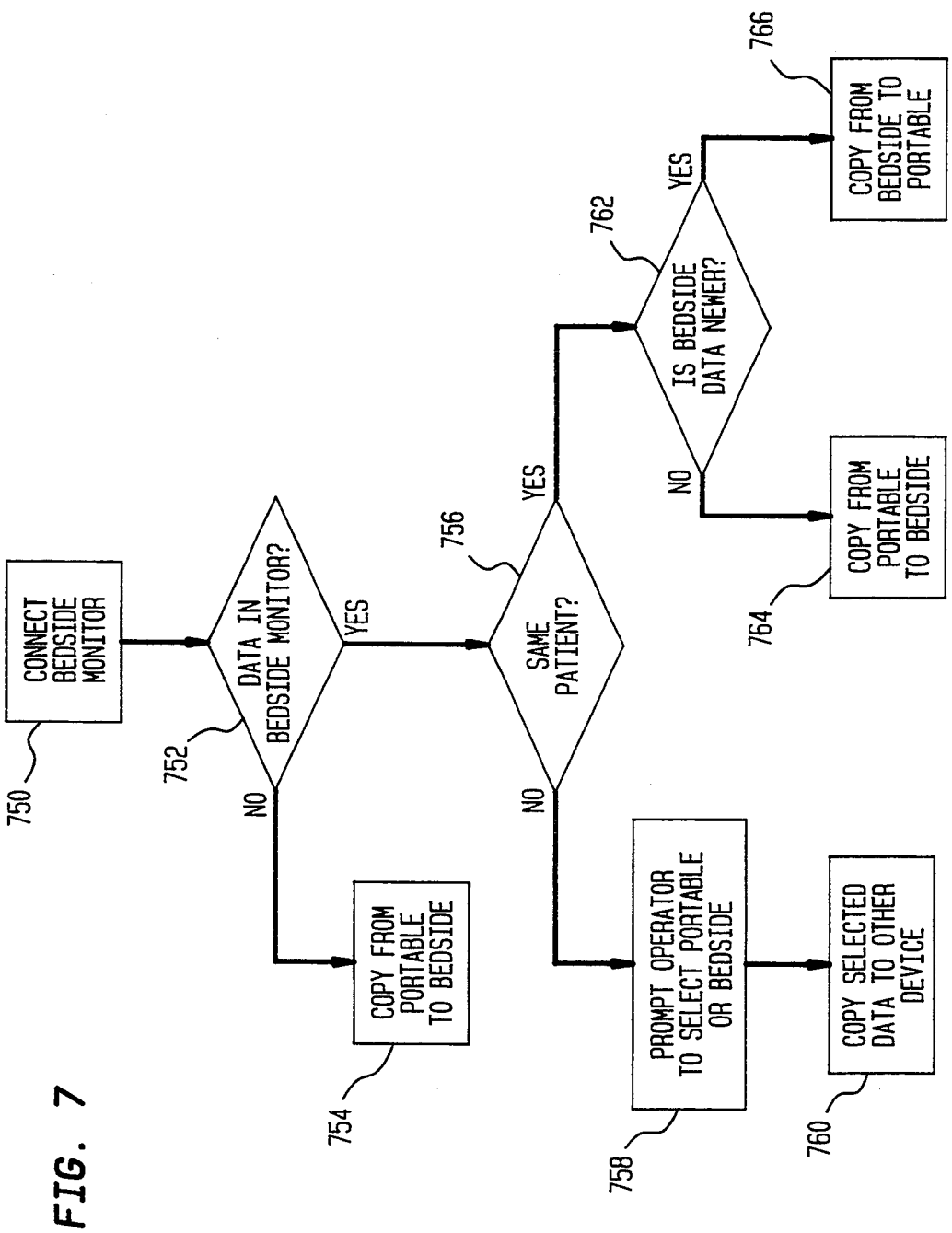

TRANSPORTABLE MODULAR PATIENT MONITOR

CROSS REFERENCE TO RELATED APPLICATIONS

The following U.S. applications which are assigned to the same assignee as the instant application and filed concurrently therewith have related subject matter: U.S. Ser. No. 07/989,414 entitled DATA ACQUISITION POD FOR A PATIENT MONITORING SYSTEM; U.S. Ser. No. 07/989,410 entitled DOCKING STATION FOR A PATIENT MONITORING SYSTEM; Ser. No. 07/989,415 entitled TRANSPORTABLE MODULAR PATIENT MONITOR WITH DATA ACQUISITION MODULES; and U.S. Ser. No. 07/989,416 entitled PRESSURE DATA ACQUISITION DEVICE FOR A PATIENT MONITORING SYSTEM.

FIELD OF THE INVENTION

The present invention relates to medical systems and in particular to patient monitoring systems for collecting, storing and displaying medical data.

BACKGROUND OF THE INVENTION

In hospitals and other health care environments, it is often necessary to continually collect and analyze a variety of medical data from a patient. These data may include electrocardiogram signals, body temperature, blood pressure, respiration, pulse and other parameters.

Monitoring systems in the related art have typically fallen into one of two general categories: multi-function monitoring, recording and displaying systems which process and collect all of the data desired, but are bulky and difficult to transport; and small, portable systems which are easy to transport, but process and collect fewer types of data and have limited storage capability. Initially (e.g., in an ambulance or an emergency room) a patient is connected to a simple, portable monitor to observe a limited number of medical attributes, such as EKG or non-invasive blood pressure. As the patient moves to higher care facilities (e.g., an intensive care unit or operating room) it is desirable to augment these simple monitors to observe additional parameters. Generally, this is accomplished by disconnecting the patient from the simple monitor and connecting the patient to a monitoring system having more robust capabilities.

The need for continuity of data collection and display is most pressing in emergency situations. Hospital personnel want to monitor additional parameters, change the selection of parameters viewed, or retrieve additional data from the patient's history. At the same time, the patient may have to move to a different care unit. During an emergency, the speed at which a patient is transferred from a bed to an operating room or intensive care unit may substantially impact the patient's chance of survival. Hospital personnel need to be able to quickly add functionality and go.

Two major considerations in the design of monitoring systems have been ease and speed of system reconfiguration. It is particularly undesirable to connect sensors to a patient or disconnect them immediately prior to transportation or administration of critical procedures. U.S. Pat. Nos. 4,715,385 and 4,895,385 to Cudahy et al. discuss a monitoring system which includes a fixed location display unit and a portable display unit. A digital acquisition and processing module (DAPM) receives data from sensors attached to the patient and provides the data to either or both of the fixed and portable display units. Normally, the DAPM is inserted into a bedside display unit located near the patient's bed. When it is necessary to reconfigure the system for transporting the patient, the DAPM is connected to the portable display and then disconnected from the bedside display. The DAPM remains attached to the patient during this reconfiguration step and during patient transport, eliminating the need to reconnect the patient to intrusive devices. Once the DAPM is disconnected from the bedside display, a transportable monitoring system is formed, comprising the portable display and DAPM.

Besides the time delays which may be encountered when adding sensors to the monitor configuration, systems in the prior art also leave much to be desired with respect to cable management. A large number of cables extend between the patient and the monitor. In the past, there has been at least one cable added for each parameter monitored. For example, there may be five cables for EKG, two for cardiac output, two for temperature, plus four hoses for measuring blood pressure using invasive sensors. This array of cables and hoses interferes with the movement of personnel around the patient's bed. The greater the number of cables and hoses, the greater the risk that someone will accidentally disrupt one of them. This has been a common problem in previous systems from several vendors.

Furthermore, the digital acquisition and processing module of the Cudahy et al. system has a fixed parameter configuration, and if the parameter requirements change due to a change in condition of the patient, the digital acquisition and processing module must be disconnected and a different module including the new parameters which are required to be monitored must be connected. This process is not only time consuming, due to the reconnection of the sensors and cables between the patient and the module, but also destructive of data since patient data acquired in the first processing module is lost when it is disconnected and is not transferred to the subsequent processing module. Furthermore, the processing module of Cudahy et al. is extremely bulky and difficult to position near a patient. In order to use the fixed display to observe data from the DAPM, the DAPM must be inserted into the fixed display. And furthermore, the processing module of Cudahy et al. requires extensive cabling to the different patient sensors, which further adds to the complexity and setup time of the system.

Additional simplification of the steps performed to reconfigure the system is also desirable in order to reduce the time to prepare the patient and monitoring system for transportation to an operating room or intensive care unit.

SUMMARY OF THE INVENTION

The present invention is embodied in patient monitoring apparatus for display on a display device of patient data. The apparatus is adapted for use in a system which includes a plurality of sensors. The data are collected from a medical patient using the plurality of sensors.

The apparatus includes a docking station.

At least one data acquisition module selectively communicates with the plurality of sensors. The data acquisition module is adapted for collecting patient data from the sensors and transmitting digital data produced from the patient data.

A portable monitor is detachably coupled to the data acquisition module for receiving the digital data and storing the digital data. The portable monitor is detachably coupled to the docking station. The portable monitor receives power from the docking station and transmits data to the docking station.

BRIEF DESCRIPTION OF THE DRAWINGS

FIG. 1b is an isometric view of the patient monitoring system shown in FIG. 1a.

FIG. 2 is a block diagram of a printed circuit board within the patient monitoring system shown in FIG. 1a.

FIG. 3 is a block diagram of a printed circuit board within the patient monitoring system shown in FIG. 1a.

FIG. 4 is a block diagram of a data acquisition pod shown in FIG. 1a.

FIG. 5 is an isometric view of a cartridge shown in FIG. 1a.

FIG. 6 is an isometric view of the docking station shown in FIG. 1a.

FIG. 7 is a flow diagram of the memory update process used in the system shown in FIG. 1a.

DESCRIPTION OF THE EXEMPLARY EMBODIMENT

OVERVIEW

Figure 1A:
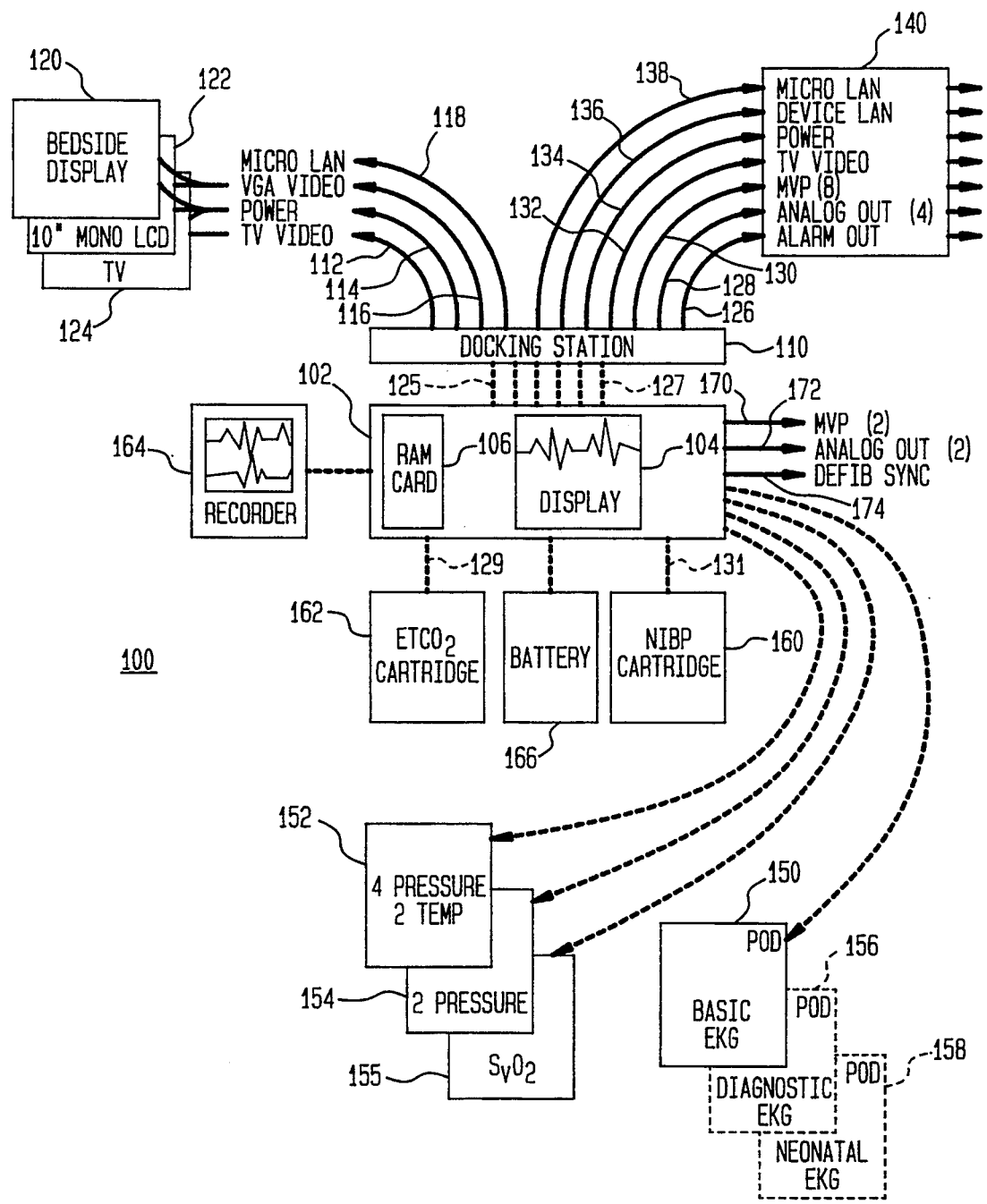
FIG. 1a is a block diagram of an exemplary patient monitoring system in accordance with the invention.

An exemplary portable monitor assembly 100 in accordance with the present invention is shown in FIG. 1a. A portable monitor 102 is detachably coupled to and acquires physiological data signals from a plurality of data acquisition modules. The data acquisition modules include data acquisition pods 150, 152, 154, 155, 156 and 158 and data acquisition cartridges 160 and 162. The pod basically combines the patient data into a single output signal, whereas the cartridges combine patient data and may also include signal processing and sensor support devices. The pods 150–158 are advantageously small, and may be placed in a variety of locations, providing a high degree of flexibility to medical personnel. The pods 150–158 provide cable management capability because each pod is connected to monitor 102 by, at most, one cable, regardless of how many sensors are coupled to the pod. The pods 150–158 and cartridges 160 and 162 may be attached to both invasive and noninvasive sensors (not shown) for collecting physiological data from a patient. As used herein, the detachable coupling of the data acquisition modules, and in particular for pods 150–156, is intended to include any manner of communicating the acquired data signals to monitor 102, such as a wireless communication link.

Many prior art systems required insertion of the cartridges (modules) into a bulky box or into a display. The data acquisition pods in the present invention are standalone (self-contained) devices. In addition, they connect directly to case 103 of the portable monitor 102. There is no need to insert the pods into a bulky box, or into a display unit, to display data. As a result the monitor-pod configuration need not be changed to transport the patient. No additional connections need be established between the monitor and the pods, and no connections need be detached.

Pods 150–158 and cartridges 160 and 162 may be connected to portable monitor 102 independently of one another. To add function to the monitoring system for a higher level of care, an additional pod 150–158 or cartridge 160 or 162 may be added without affecting any other modules that are already coupled to monitor 102. There is no need to reconfigure the entire system to add a module.

Pods 150–158 are independently positionable, both from one another, and from monitor 102. In accordance with the present invention, pods 150–158 may be placed in any convenient location close to the patient. Each pod may be placed at a different location if desired, to minimize the lengths of the cables and hoses connecting the patient to the respective pods. Alternatively, the pods may be collocated, so that all of the cables and hoses are confined to a single region. Either method enhances cable management.

The portable monitor 102 displays the physiological data and includes means for detachably mounting data acquisition cartridges, which may include a Non-Invasive Blood Pressure (NIBP) cartridge 160 and/or an end-tidal cartridge 162 (for measuring airway carbon dioxide). A three channel recorder 164, and a battery pack 166 may also be detachably connected to portable monitor 102. Each device 160–166 is configured to provide both electrical and mechanical couplings when the device is mounted on the monitor 102. Each cartridge 160 and 162 and recorder 166 provide their own return circuits with 5000 volts isolation from the portable monitor ground, to prevent current flow from the patient to earth ground by way of the cartridge and monitor 102. The portable monitor 102 has a user-accessible slot for one random access memory card (or RAM card) 106 which allows easy removal and storage of patient data, such as demographic and physiological trend data. The memory card may also be used to transfer replacement software instructions to the portable monitor.

Each pod 150–158 receives analog data signals from a plurality of sensors, and combines the data from the plurality of sensors into a combined analog data signal. The combined analog data signal is then converted to a digital output channel which is coupled to portable monitor 102. By channeling patient data signals from many sensors into a single cable for transfer to monitor 102, the desired cable management is achieved. For example, if pod 150 is located at or on the bed, the number of cables between the bed and monitor 102 is reduced from eight to one.

A base EKG pod 150 provides connections for a five electrode (7 lead) EKG, one connection for a pulse oximetry ($SpO_2$) sensor, and two multifunction receptacles for measuring temperature, impedance respiration and/or cardiac output.

In the exemplary embodiment, two special purpose pods are available as alternatives to pod 150. A diagnostic pod 156 accepts data from the same sensors as base pod 150, and also has five extra leads which may be used for EEG or for a 12 lead EKG. A neonatal pod 158 has input terminals for the same types of data as diagnostic pod 156, plus an additional terminal for a transcutaneous oxygen or carbon dioxide sensor. Pod 152 includes channels for mounting four pressure transducers and two additional temperature sensors. Alternatively, Pod 154 may be used to collect data from two pressure transducers. Catheter Pod 155 provides oximetry data ($SvO_2$). Further pods performing different functions may optionally be added and would be understood by those skilled in the art.

In accordance with one aspect of the invention, portable monitor 102 is detachably coupled to a docking station 110 which may be positioned near the patient's bed (e.g., on the bed, a bed rail, a wall, an intravenous pole or a shelf). In accordance with another aspect of the invention, portable monitor 102 and docking station 110 provide complementary services. Monitoring devices which attach to the patient's body or are transported with the patient are coupled to the portable monitor 102; whereas devices and services which are fixed in the room or are to be made continuously available in the room are coupled to the docking station.

The docking station 110 provides portable monitor 102 with a full suite of power and communications services. These services allow portable monitor 102 to perform functions previously performed primarily through the use of large, fixed monitoring systems. At the same time, the simple connection between the docking station 110 and monitor 102 allows rapid disconnection of monitor 102 for transporting the patient. The user merely picks up monitor 102 from docking station 110 to prepare monitor 102 for transport. Docking station 110 recharges the battery of monitor 102 while the monitor is in the docking station, so that in most instances, it is not even necessary to install a battery pack to transport the patient.

Docking station 110 provides mechanical support for mounting the portable monitor 102, as well as electrical couplings to a remote display device 120 (typically a bedside display), power 114, large display 122, and television display 124. Remote display device 120 may be a fully functioning monitor including processing and display functions, or just a slave display receiving signals from the docking station for display. Docking Station 110 can also communicate with several local area networks (LANs). Docking station 110 provides a simple mechanism to connect portable monitor 102 with several devices and networks without the need to connect individual cables. Data and power connectors on docking station 110 and on the case 103 of portable monitor 102 allow physical and electrical connections to be established concurrently. Although docking station 110 may be coupled to networks and remote stations outside of the patient's room, docking station need not mount on the wall to connect to these networks and stations. Docking station 110 may be connected to a wallbox 140 to provide the additional communications links.

Although the portable monitor 102 as described in the exemplary embodiment performs the functions of a multi-function bedside monitor when attached to docking station 110, it may be desirable to use the portable monitor 102 in conjunction with an additional remote display 120. For example, in the operating room, the remote display 120 may be a slave display so as to provide a larger or more easily readable display. The remote display 120 may be a conventional, fully functioning bedside patient monitoring unit which receives, stores, displays and transmits medical data. Alternately, the remote display 120 may be an intelligent workstation with a VGA display and conventional disk storage. The portable monitor 102 also includes a port 127 for optionally connecting the portable monitor directly to a remote display 120 when the portable monitor is not in docking station 110.

Upon establishment of a connection between portable monitor 102 and docking station 110, assembly 102 determines whether the most recent physiological data for the patient is stored in the assembly or in a remote display 120 coupled to docking station 110. The more recent data are then copied to the device (display monitor 102 or remote display 120) having the less recent data (assuming that the remote display 120 has processing capability). A conventional memory card 106 (shown in FIG. 2), is used to transfer data between the portable monitor 102 and the remote display 120. It is understood by those skilled in the art that, as an alternative to using a memory card for data transfers, the data may be directly transferred by a communications link.

Once the portable monitor 102 is coupled to the remote display 120, and the data in the two monitors are synchronized by the memory card 106 transfer discussed above, all patient data received by the portable monitor 102 are transferred to the remote display 120. In this manner, patient data are stored redundantly in remote display 120 and portable monitor 102. The patient can be switched from one portable monitor 102 to another 102' (not shown) by transferring the memory card to the second portable monitor 102' and from one remote display 120 to another 120' (not shown) without any loss of data, or any break in the continuity of the data.

According to another aspect of the invention, display setup data are stored in portable monitor 102. The setup data are used to define which waveforms and which parameters appear in the available screen areas. Unlike the systems in the prior art, the setup data in monitor 102 are independent of which sensors are furnishing data, or which display is used (Whereas in the prior art, the setup data were typically stored in the display and were entered by the user each time a new display was attached to the monitor). The setup data are applied when the display is coupled to monitor 102 and turned on. If the display is configured to display the waveform being monitored, portable monitor 102 places the data in the appropriate areas of the display. If the display is not configured to display the waveform, then it is not displayed until the user selects the waveform on the display.

Figure 1B:
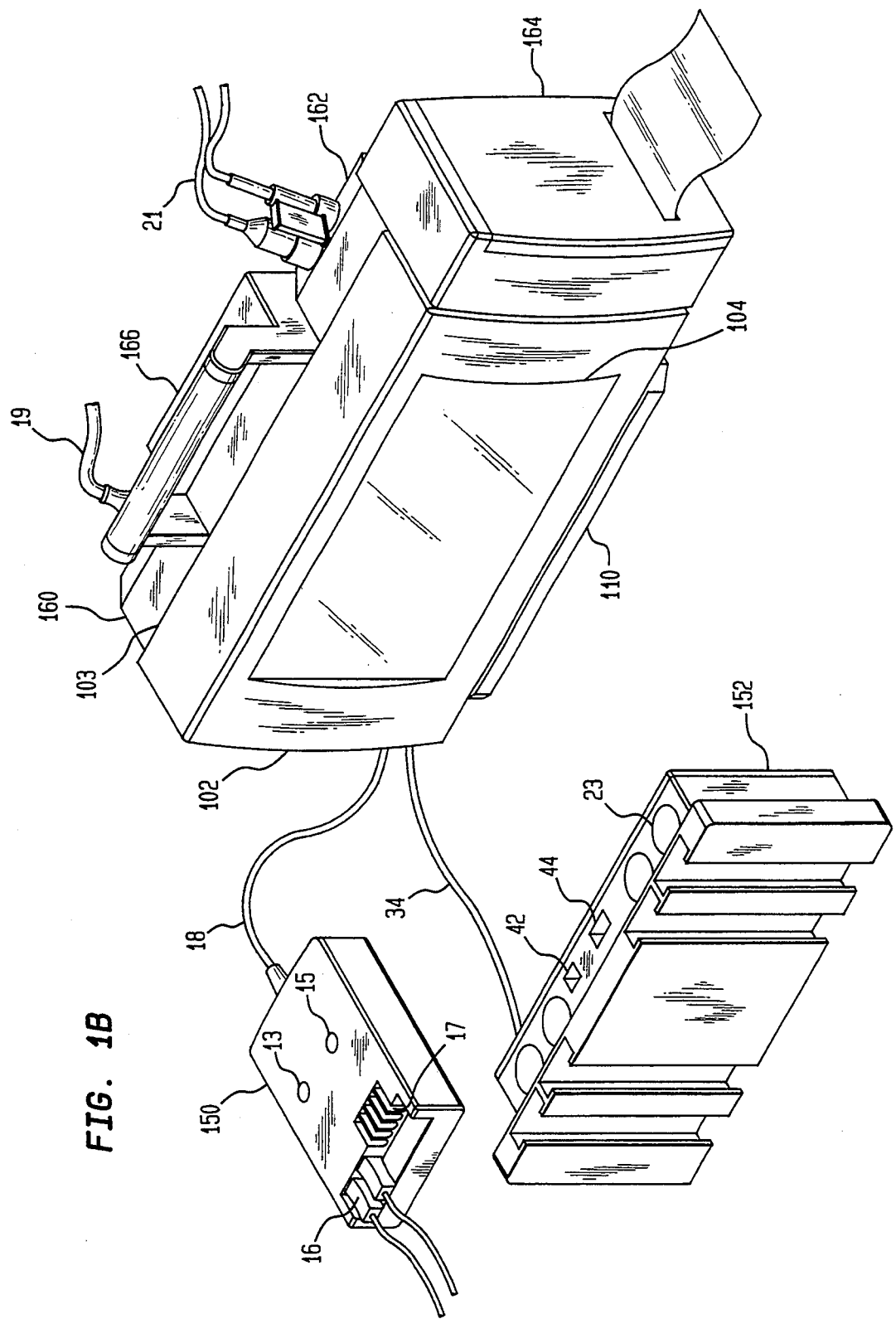

FIG. 1b shows the physical configuration of the monitor assembly 100 of FIG. 1a. Portable monitor 102 is mounted on docking station 110, providing physical support, power, and communications. Monitor 102 acquires physiological data signals from data acquisition pods 150 for EKG data and 152 for pressure data. The Non-invasive blood pressure cartridge 160, the end tidal $CO_2$ cartridge 162, a hardcopy output device such as recorder 164 and the battery back 166 are individually attached to portable monitor 102 for purposes of illustration.

DETAILED DESCRIPTION PORTABLE MONITOR

As shown in FIGS. 1a and 1b, portable monitor 102 is the core of a modular patient monitoring system 100. Portable monitor 102 includes an integrated liquid crystal display (LCD) 104. Peripheral devices may be coupled to the portable monitor 102, including input devices (e.g., pods 150, 152, 154, 155, 156, 158 and cartridges 160 and 162) and output devices (e.g., recorder 164 and cathode ray tube (CRT) display 120 and LCD 122). A possible minimum configuration of the exemplary embodiment includes portable monitor 102, an EKG pod (150, 156 or 158) and the battery pack 166. Additional pods (152, 154 and/or 155) and cartridges (160, 162) may be substituted or added, depending on the types of trend data desired for each specific patient. Portable monitor 102 may be directly connected to additional external displays 120 and 122 through analog output ports 172. Alternatively, portable monitor 102 may be detachably mounted on a docking station 110 which provides couplings to power and communications networks. Portable monitor 102 receives power from docking station 110 through a connector 125.

Figure 2:
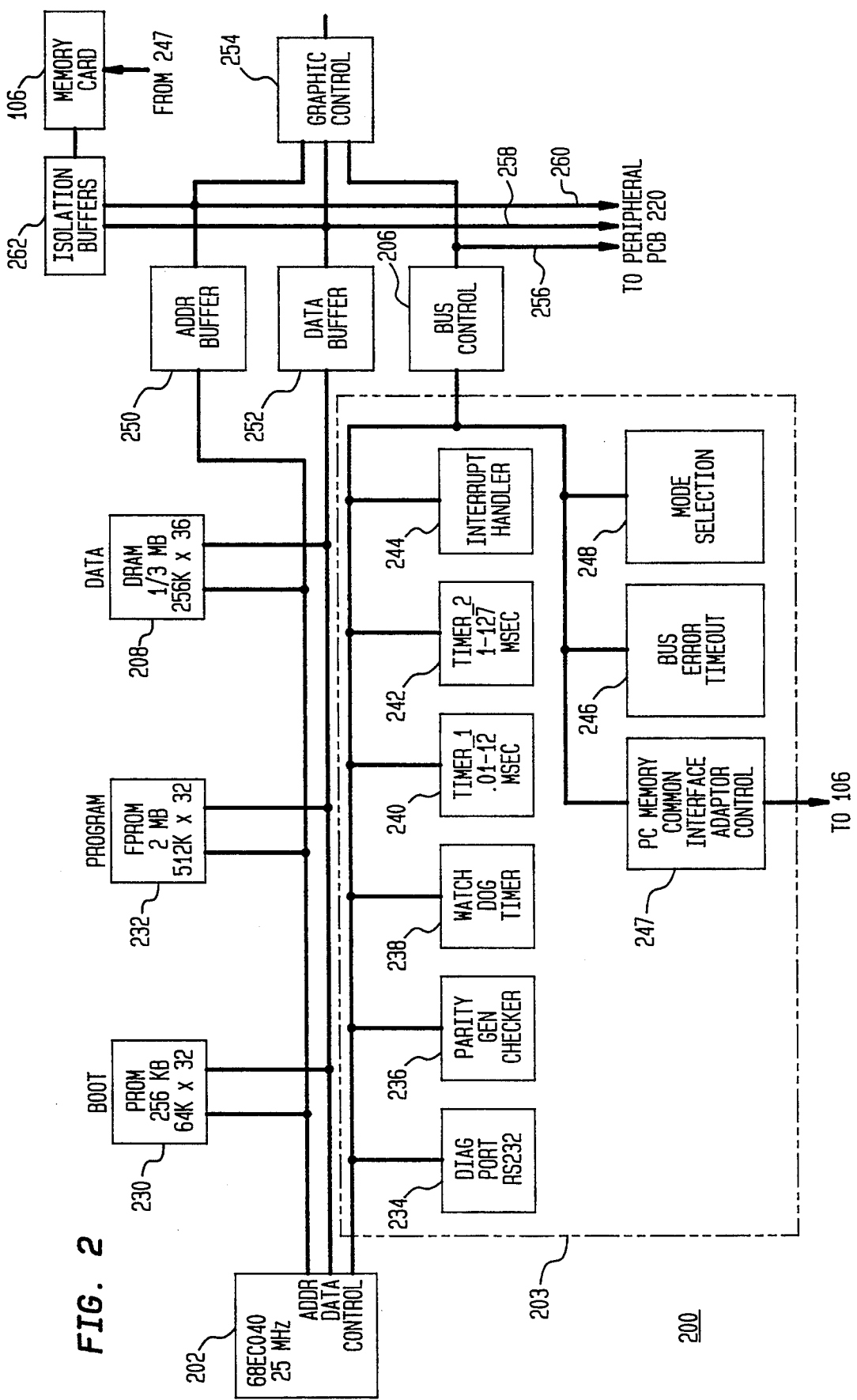

FIG. 2 is a block diagram showing the interaction of the components of portable monitor 102. Portable monitor 102 includes two printed circuit boards (PCBs): a processor PCB 200 and a peripheral PCB 220. Processor PCB 200 provides processing and storage resources for algorithm computation and for controlling system operations. In conjunction with peripheral printed circuit board (PCB) 220, Processor PCB 200 controls the acquisition of data from the pods and cartridges, the processing of patient data, display of parameters and waveforms, alarms and Ethernet TM and multi-vendor connectivity.

Processor 202 may be a Motorola 68EC040 or comparable processor. It controls the operation of portable monitor 102 and performs the non-numerically intensive arithmetic computations. Some numerically intensive computations are performed by components on peripheral PCB 220, and are discussed below. A 32 bit processor bus, which may be Multibus II, provides the processor 202 access to the other devices on the processor PCB 200.

Three memory systems are located on the processor PCB 200. A boot erasable programmable read only memory (EPROM) 230 provides the initial program startup, system console support, and the method to erase and download software into the flash EPROM (FPROM) 232. The EPROM may include 27C1024, 27C2048 or 27C4096 devices, which allow two wait state operation for the processor 202. The EPROM has a total memory size of 256 KB to 1 MB, with 32 bit access.

Flash EPROM 232 contains the executable code. Flash EPROM 232 is programmed on processor PCB 200 under the control of processor 202. Flash EPROM 232 may include AMD/NEC 28F020 or 28F040 devices, which allow two wait state operation. Flash EPROM has a total memory size of 2 to 4 MB of memory, with 32 bit access. Flash EPROM 232 supports a line burst fill mode of operation.

A dynamic random access memory (DRAM) 208 provides program data space. The system may also be set to a development mode, in which executable code is placed in DRAM 208. DRAM 208 may include NEC D424190 or HM514280 devices, which allow 2 wait state operation. The DRAM 208 has a total memory size of 1 MB of memory. The memory is organized as 32 data bits and 4 parity bits.

Processor PCB 200 includes support circuitry 203 for processor 202. Circuitry 203 includes: DRAM parity generation and checking 236; two interval timers 240 and 242; a watchdog timer 238, an interrupt handler 244, a serial diagnostic port 234, memory mode selection 248, bus error time-out 246 and PC memory common interface adaptor control 247. In the exemplary embodiment, support circuitry 203 is implemented in application specific integrated circuits (ASIC).

Parity circuit 236 generates odd parity on memory writes and checks for errors on memory reads. If an error is detected, a parity error flag is set on a byte basis.

Two interval timers 240 and 242 are provided for time measurement. The first timer 240 has a range of 0.1 to 12.7 milliseconds (msec). The second timer 242 has a range of 1 to 127 msec. The user selects the interval for each timer. If either timer is enabled and counts to the specified interval, an interrupt flag is set.

Watchdog timer 238 allows selection of a timeout interval between 0.01 and 1.27 seconds. The user selects the interval. During system startup, watchdog timer 238 is disabled. If timer 238 is enabled and counts to the specified value during execution of any process, an interrupt flag is set. If the interrupt is not serviced within predetermined interval, a processor reset is generated.

Interrupt handler 244 prioritizes the various interrupt sources into seven levels for the processor. The interrupts may be generated by watchdog timer 238, parity checker 236, timer 240, peripheral PCB 220, timer 242, graphics controller 254, or diagnostic port 234.

Diagnostic serial port 234 provides a receive and transmit communications channel at 1.2, 9.6, or 19.2 Kbits per second, with 8 data bits, no parity, and 1 stop bit. The choice of the data rate is determined by a programmable parameter value. Data transfers are supported by polled status and interrupt control. Internal loopback may be programmed.

Memory mode selection 248 controls the allocation of normal program execution space to the three physical memory devices: boot EPROM 230, flash PROM 232 and DRAM 208. During system startup, the execution space is allocated on boot EPROM 230.

The bus error time-out function 246 activates a 10 microsecond timer when a bus cycle starts. The bus error is activated if a data acknowledge signal is not received within the 10 microsecond time period.

Figure 3:
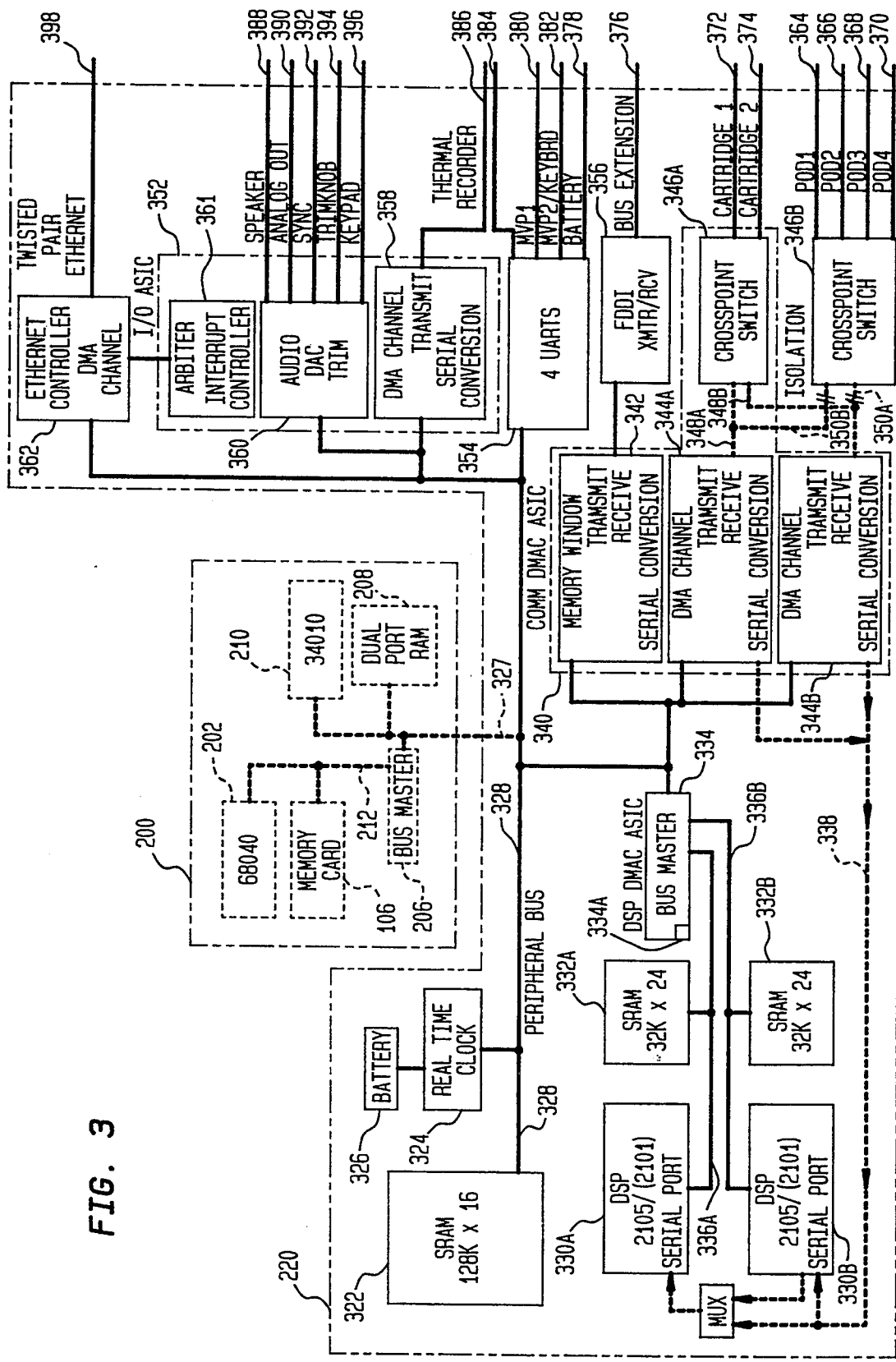

Bus master circuit 206 on processor PCB 200 maps a 16 Mbyte peripheral space into the address space of CPU 202. In the exemplary embodiment, CPU 202 has a 32 bit data bus 212 and peripheral bus 328 (as shown in FIG. 3) includes a 16 bit data bus. In order to accommodate the different bus data paths, bus master 206 includes a circuit to split each 32 bit word received from CPU 202 into two 16 bit words which peripheral bus 328 can accept. Each pair of 16 bit words is transmitted over two peripheral bus cycles.

A conventional random access memory card 106 is used for information storage and transfer. The memory card 106 interface is controlled by the PC memory common interface adapter control function 247 in ASIC 203. Memory card 106 is a credit card sized encapsulated circuit board containing static RAM and a small battery. The information stored in the memory card 106 includes setup data (e.g., alarm limits), patient specific demographic and physiological trend data, and software.

Typically, memory card 106 will be used when transferring patient data between two different portable monitors 102. Such transfers typically occur when a patient moves from one care unit (e.g., intensive care unit, operating room, or recovery room) to another. When used for storing software, memory card 106 provides a convenient mechanism for downloading software upgrades to portable monitor 102, which are then stored in a flash EPROM 232, shown in FIG. 3. When used for these purposes, memory card 106 may be removed from portable monitor 102, except when in use for data or software transfers.

Another possible use of memory card 106 may be to associate a respective card with each patient from admission to checkout, providing rapid access to the patient's history at any time during his or her stay in the hospital. When used for this purpose, memory card 106 may remain in portable monitor 102 at all times between patient admission and discharge, except when the card is transferred between two portable monitors. All patient trend data would be stored, in a particular memory card and continuously upgraded at appropriate intervals.

Still another use for the memory card is for software maintenance and upgrades. A new (second) set of instructions may be downloaded to the Flash EPROM 232 from the memory card 106 to replace the existing (first) set of instructions.

FIG. 3 is a block diagram of peripheral PCB 220 shown in FIG. 2. Peripheral PCB 220 manages the interfaces between portable monitor 102 and all external devices and networks to which it may be connected. Peripheral PCB 220 is coupled to a port 327 of processor PCB 200. A peripheral bus 328, which may use conventional Intel Multibus format, couples processor 202 and the devices on the peripheral PCB 220. Peripheral bus 328 includes a 16-bit data path and a 24-bit address space, and has a bandwidth of at least 8 Mbytes/second.

Multiple bus masters can access peripheral bus 328, under the control of an arbiter 361, described below. The bus masters include: host bus master 206 for processor 202; two digital signal processors (DSPs) 330a and 330b for preprocessing the data acquisition samples; a carrier sense multiple access/collision detection (CSMA/CD) controller direct memory access (DMA) channel 362; two DMA channels 344a and 344b for transmitting commands to pods 150–158 and cartridges 160, 162 and for receiving sample data from the pods and cartridges; and a DMA channel for transmitting data to thermal recorder 164. When one of these bus masters (which may be either 206, 334, 362, 344a, 344b or 358) uses bus 328, processor 202 gives permission and releases control of address, data and strobe lines (not shown) in the bus 328. The bus master 206, 334, 344a, 344b, 358 or 362 then places memory addresses on bus 328, directing DMA data transfers to send or receive data.

The DSP DMA control is implemented in a bus master application specific integrated circuit (ASIC) 334. Bus master circuit 334 connected to the DSPs 330a and 330b allows the DSPs to access the entire memory space 322 via peripheral bus 328. DSPs 330a and 330b access bus 328 by an indirect method. The DSP first writes to an address register 334a in bus master 334. This address points to the desired address on peripheral bus 328. After loading the address, the DSP may write to locations on bus 328. After each word is written, the lower sixteen address lines (not shown) will automatically increment, allowing efficient moves of block data.

Bus Master 334 may also operate in slave mode, allowing the CPU 202 to arbitrate DSPs' 330a and 330b communications with peripheral bus 328. In this mode, CPU 202 can write directly into the DSPs' static random access memories (SRAM) 332a and 332b. This capability is used during initial download of the DSP code from CPU flash programmable read only memory (FPROM) 232 as shown in FIG. 2. CPU 202 may also use this capability to deposit variables to and retrieve variables from DSPs 330a and 330b. All other bus masters (DMA channels 344a, 344b, 358 and 362) are prevented from accessing the DSPs' SRAM 332a and 332b in this manner, to ensure the integrity of the DSP code.

DMA channels 344a, 344b, 358 and 362 use peripheral bus 328 to read and write shared SRAM memory 322 and peripherals 150, 152, 154, 155, 156, 158, 160, 162, and 164. Channels 344a and 344b are used for data acquisition from pods 150, 152, 154, 155, 156, 158 and/or cartridges 160, 162. Channels 344a, 344b send commands and timing information to the pods and cartridges, and receive data and status from them.

When receiving data, channels 344a, 344b write the received data to respective buffers every two milliseconds (msec). After five consecutive two msec cycles, the data in the buffers are written over with new data. To ensure transfer of the data to the shared memory 322 for storage, two different types of interrupts are generated within channels 344a and 344b. The first interrupt is generated every two msec when data are placed in the buffer. The second interrupt is generated each time five blocks of data are received, i.e., every ten msec.

DMA channel 358 is a special purpose thermal head driver for recorder 164. This channel combines data from three different locations in shared memory 322 to overlay grid, text and waveform data. Channel 358 also chains together print pages of varying length for outputting the data to recorder 164. The output signal from channel 358 is sent over a serial link 386 to recorder 164.

DMA channel 362 is a conventional single chip CSMA/CD controller for twisted pair cable. This channel is used for communications to LANs when portable monitor 102 is placed in a docking station 110. Channel 362 is not operated when portable monitor 102 is removed from docking station 110.

Data are received from the pods and cartridges by way of two cross point switches 346a and 346b. All pod connections are through switch 346b, which provides a 5000 volt isolation between the sensor return circuits and portable monitor 102 ground to guard against ground loops, which could endanger patient safety and introduce noise into the measured data. In the exemplary embodiment, crosspoint switch 346a does not provide this isolation, so cartridges 160, 162 provide their own 5000 volt isolation between cartridge return circuits and the portable monitor 102 ground. Otherwise the two crosspoint switches 346a and 346b are functionally and logically identical.

The crosspoint switches 346a, 346b receive patient data signals from the pods and cartridges and multiplex the data signals before passing them on to channels 344a and 344b. Each switch 346a and 346b can communicate with either channel 344a or 344b via separate 1.6 Mhz links 348a, 348b, 350a, and 350b.

The two DMA channels 344a and 344b are synchronous and are run in a master/slave configuration. Every 15.6 microseconds, there are transfers between the pods/cartridges and shared memory 322. These transfers include two reads (one per channel 344a and 344b) and two writes (one per channel 344a and 344b) to a shared memory 322. Shared memory 322 includes an extra two byte word for channels 344a and 344b that is fetched during each 15 microsecond transfer to configure the crosspoint switches 346a and 346b. The low byte is used to control the crosspoint switch of slave DMA channel 344b and the high byte is used to control master DMA channel 344a. For each respective pod port 364, 366, 368, 370 and cartridge port 372, 374, one respective bit in the control word is used to enable power to the pod, and another respective bit is used to enable transmission of a sync signal to the pod. Thus a total of five words are transferred during each 15 msec cycle. The data samples are interleaved between the two DMA channels 344a and 344b.

To allow modifications to the configuration of pods and cartridges, CPU 202 issues a request for identification to the pods and cartridges by way of their respective ports 364, 366, 368, 370, 372 and 374. The pod or cartridge responds with a unique identification signal.

When commanding the pods and cartridges, the channels 344a and 344b fetch 24 bit words from shared memory 322. Each 24 bit word includes an 8-bit DMA control word and a 16-bit front end command. The 8-bit DMA control word includes a 3-bit slot address identifying the port 364, 366, 368, 370, 372 and 374 to which the command is routed and a 2-bit DSP redirection control to identify the routing of the data returned by the pod or cartridge. The 16-bit command is transferred to the pods/cartridges.

The DMA channels 344a and 344b also communicate with DSPs 330a and 330b by way of a serial interface 338. All of the data received by channels 344a and 344b is routed to the DSPs in addition to shared memory 322. The DSP is sent a frame sync signal from master DMA channel 344a every 2 msec.

A bus arbiter 352 controls access to bus master 334 and DMA channels 344a and 344b. Bus master circuit 334 provides both round robin and prioritized arbitration. Since DMA channels 344a and 344b could lose data if denied access to bus 328 for an extended period, a round robin element is included in the arbitration scheme. Within the timing constraints that prevent loss of data, bus arbiter 352 also allows burst mode operation, allowing multiple words to be written without entering additional wait states. Bus arbiter 352 also allows burst mode operation during read cycles.

In addition to the bus masters, there are also slave devices coupled to bus 328 by universal asynchronous receiver/transmitters (UARTs) 354. These include two multivendor ports 380 and 382 (MVP1, MVP2 respectively), and a battery port 378.

The two DSPs 330a and 330b may be conventional processors such as Analog Devices ADSP 2101 or 2105 DSP chips. These are 16-bit processors with an instruction set which includes normalization and exponent derivation by barrel shifting. Since many of the operations performed in the EKG algorithms are common signal processing functions, most of the computationally intensive and simply defined processing stages may be performed in the DSPs. These stages may include finite impulse response (FIR) and infinite impulse response (IIR) filtering, cross-correlation, power spectrum estimation and others. Matrix algorithms and other numerical processing may also be performed in the DSPs.

In addition to performing signal processing tasks, DSPs 330a and 330b distribute data to all of the output devices coupled to portable monitor 102, including local display devices and network devices. The DSPs perform appropriate sample rate conversion, data scaling, and offsetting to the raw sample data collected by monitor 102.

Monitor 102 includes a small internal battery (not shown). If external battery 166 (shown in FIG. 1b) is at a low charge level, the internal battery provides power for a time period (e.g., 1 minute) which is sufficient to remove battery 166 and install another external battery.

DATA ACQUISITION PODS

Figure 4:
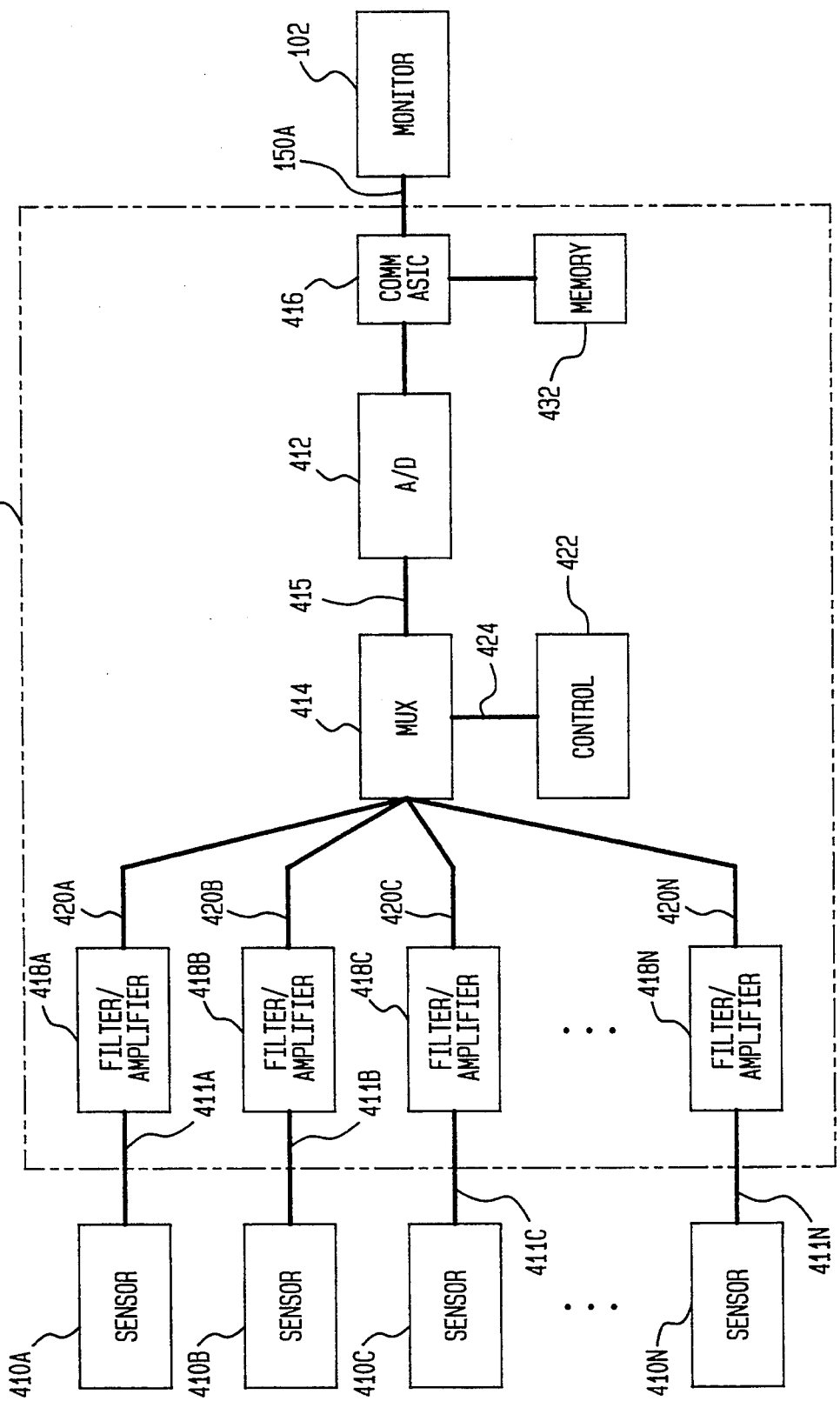

FIG. 4 shows a block diagram of an exemplary data acquisition pod 150. Pod 150 is self-contained. That is, Pod 150 includes all of the electronics required to acquire a signal from a sensor, condition the signal and transmit the signal to portable monitor 102, without inserting pod 150 in the monitor 102, or in a box (Pod 150 is unlike prior art data acquisition cartridges which must be mechanically inserted into a separate box to couple with the monitoring system). The use of a self-contained, standalone pod 150 simplifies preparing the patient for transportation. There is no need to remove pod 150 from a box, or to reconnect any cables between the pod 150 and monitor 102.

Pod 150 receives patient data from a plurality of sensors 410a–410n via terminals 411a–411n (or terminals 16 and 17 shown in FIG. 1). These sensors may measure EKG, blood pressure, pulse, temperature, EEG or other physiological parameters. Each input data stream is amplified and filtered by circuits 418a–418n to remove noise and any undesirable signals which the sensors may acquire. The amplified and filtered output signals 420a–420d are combined to form a single signal 415 by a combiner which may be a time division multiplexer 414. The combined signal 415 is then converted from analog form to digital form by A/D converter 412. Pod 150 includes a single coupling 150a to portable monitor 102. Signals are transmitted to coupling 150a by way of a communications ASIC, 416. Pod 150 may also optionally include a memory 432 for storing calibration data and alarm limits. Pods 152, 154, 155, 156 and 158 are similar insofar as the functions shown in FIG. 4 are concerned.

The main function of the pods 150–158 is data acquisition. The filtering and amplification are performed to ensure that the data furnished to monitor 102 accurately represent the parameters sensed by sensors 410a–410n. The application of mathematical algorithms to these data to process the signals is performed inside portable monitor 102. This division of services between pods 150–158 and monitor 102 reduces the size of the pods 150–158 relative to typical prior art data acquisition cartridges. Pods 150–158 are small enough to be positioned conveniently in a variety of positions, including: on a shelf, on a bed, on a bed rail or headboard, under a pillow, or on an intravenous pole.

An exemplary patient monitoring system in accordance with the invention (shown in FIG. 1a) may include any one of a basic, diagnostic or neonatal pod. A base EKG pod 150 acquires real-time EKG and respiration waveforms as input data, which are processed by QRS, arrhythmia and S-T segment analysis algorithms in DSP's 330a and 330b. The sensors (not shown) in pod 150 are five electrodes with leads I, II, III, IV (AVR, AVL and AVF leads) and V (chest). From this data, portable monitor 102 can determine impedance respiration as well as heart rate.

Base pod 150 also accepts input data from two temperature sensors which may be used for measuring nasal respiration and cardiac output (C.O.). A nasal respiration thermistor (not shown) may be used to detect respiration by sensing the changes in nasal passage temperature due to the difference in temperature between inhaled and exhaled air. C.O. data are acquired by using the thermodilution method. An Edwards type catheter (not shown) can be used to inject either cooled or room temperature water into the coronary artery. Downstream blood temperature and injectate temperatures are then measured.

Lastly, pod 150 receives data representative of pulse and oximetry. Oximetry data representing the saturation, or fraction of oxyhemoglobin to functional hemoglobin ($SpO_2$ in $\%O_2$) are collected using absorption spectrophotometry.

As shown in FIG. 1b, pod 150 includes two proximately located switches 13 and 15. Switch 13 is coupled to a circuit which transmits a signal to monitor 102 causing monitor 102 to condition itself to start the cardiac output procedure (e.g., perform range and alarm limit adjustments). The operator actuates switch 13 at the same time that he or she injects the injectate into the patient for cardiac output measurement. The DSPs 330a and 330b in monitor 102 calculate the waveform of the temperature gradient between thermistors for the cardiac output procedure. Similarly, switch 15 is coupled to a circuit which transmits a signal to monitor 102 causing monitor 102 to configure itself to start the wedge procedure and/or switch the display to wedge mode. The operator actuates switch 15 at the same time that he or she inflates a balloon inside the patient's pulmonary artery for pulmonary artery wedge pressure measurement. Switches 13 and 15 are conveniently co-located on pod 150 (near the sensors on the patient). This facilitates concurrent actuation of switch 13 while starting the cardiac output measurement, and facilitates concurrent actuation of switch 15 while starting the wedge procedure.

Systems in the prior art typically featured the cardiac output switch 13 and wedge switch 15 on the monitor 102. It is more convenient to locate switches 13 and 15 close to the patient (as in the present invention) than on monitor 102 (as done in the prior art), because the operator is close to the patient while injecting liquid or inflating a balloon in the patient's artery. Because pod 150 is small and is easily located close to the patient, pod 150 is an advantageous device on which to locate switches 13 and 15. In some hospital room configurations, it may be desirable to place monitor 102 too far away to conveniently access monitor 102 while starting the procedures, making the switch location on pod 150 advantageous. Furthermore, safety is enhanced, because the operator does not have to walk around the lines (e.g., lines 18 and 34) connected to monitor 102.

Diagnostic pod 156 includes input terminals to receive data from sensors similar to those used in conjunction with base pod 150. In addition, the diagnostic pod accepts five further leads for receiving EKG data from additional electrodes which may be placed on the patient's chest. Alternatively, additional terminals may be used to receive EEG data.

Neonatal pod 158 includes input terminals similar to diagnostic pod 156. In addition, neonatal pod 158 includes terminals for receiving long-term, non-invasive, transcutaneous data for monitoring the partial pressures of oxygen and carbon dioxide. In addition to transcutaneous monitoring, a general gas bench for blood gas analysis may be included.

In addition to one of the above EKG pods 150, 156 or 158, an exemplary patient monitoring system in accordance with the invention may include a pressure pod 152 (or 154) and/or an oximetry catheter pod 155. Pressure pod 152 accepts data (via terminals 23) from 4 strain gage transducers (not shown), which are fluidly coupled to invasive pressure sensors, and accepts data from two temperature sensors.

Referring again to FIG. 1b, the pressure pod 152 has a zero switch 42 conveniently located on pod 152, where it is easily actuated while calibrating sensors (not shown) by exposing them to atmospheric pressure. Actuating the zero switch causes pod 152 to transmit a zero signal to monitor 102, causing monitor 102 to reset the value of its waveform to zero in response to the voltage currently detected across the sensor. A second switch 44 located on pod 152 sends a further signal to monitor 102, causing monitor 102 to condition itself to begin a wedge procedure. The response of monitor 102 to this further signal is the same as described above with respect to actuation of switch 15 on pod 150. As described above with respect to pod 150, the location of the control switches on the pod (near the patient) simplifies operations.

Pressure/Temperature pod 154 accepts data from two invasive pressure transducers. The catheter pod 155 receives data from a catheter inserted into the patients artery.

It is understood by one skilled in the art that many different embodiments of the data acquisition pod may be developed to meet different data acquisition requirements. Both the types of sensors used and the number of sensors of each type may be varied.

DATA ACQUISITION CARTRIDGES

Figure 5:
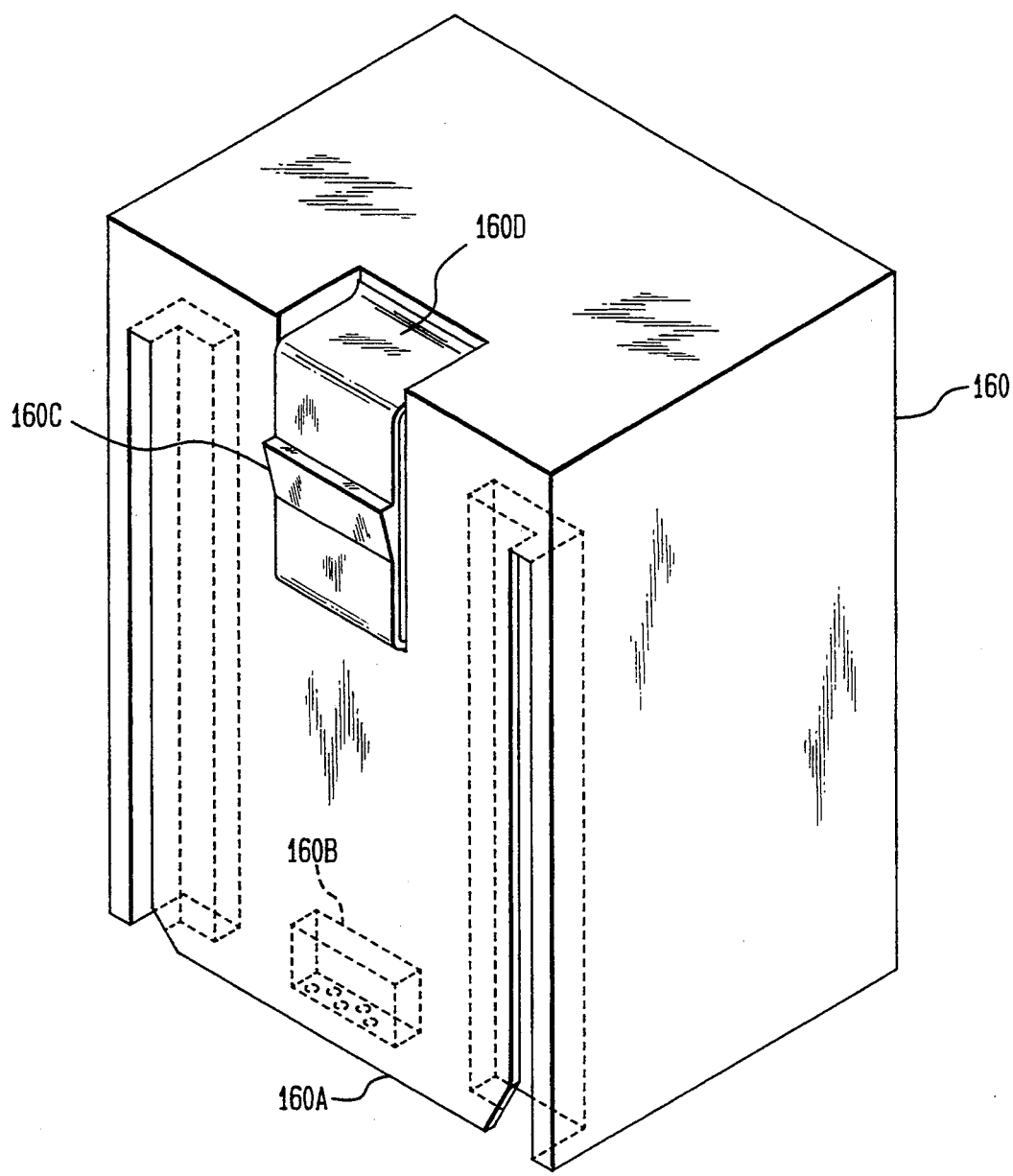

FIG. 5 shows the mechanical configuration of an exemplary non-invasive blood pressure cartridge 160. In contrast to pods 150–158, cartridge 160 is not independently positionable, but mounts on monitor 102.

Cartridge 160 accepts data via line 19 for oscillometric measurement of systolic, diastolic, and mean arterial pressures from a cuff transducer (not shown). Cartridge 160 performs functions similar to the pod functions shown in FIG. 4. In addition, the cartridge provides a separate 5000 volt isolation between the cartridge return circuit and the portable monitor ground for safety and to reduce undesirable noise.

As shown in FIG. 5, cartridge 160 includes a suitable mechanism to attach itself to portable monitor 102. This may be in the form of a guide piece 160a with a latch 160c. Guide piece 160a slides into a mating guide (not shown) on monitor 102, engaging connector 160b with connector 129 (shown in FIG. 1a) on monitor 102, and engaging the latch 160c with a mating catch (not shown) on the monitor in a single operation. Many variations in the shape of guide piece 160a and latch 160c may be used to provide the mechanical coupling at the same time that connector 160b is engaged to provide electrical coupling. Mounting cartridge 160 directly to monitor 102 is convenient and uses space efficiently; a bulky box is not needed to house the cartridge.

The end-tidal $CO_2$ Cartridge 162, recorder 164 and battery pack 166 each use a similar coupling technique, to facilitate reconfiguration of the portable monitor 102. The end-tidal $CO_2$ Cartridge 162 receives data representing inhaled and exhaled carbon dioxide partial pressures from an airway adapter via line 21 and engages connector 131 (shown in FIG. 1). The recorder 164 is a conventional three channel thermal printer. The battery pack 166 includes a conventional nickel-cadmium battery.

As with the data acquisition pods, the data acquisition cartridge may be practiced in a number of alternative embodiments. Both the types of sensors used and the number of sensors of each type may be varied. Preferably, data acquisition modules which are bulky, heavy, or consume large amounts of power are implemented as cartridges, while small, lightweight low power data acquisition modules are implemented as pods. For example, pressure cartridge 160 includes a motor and pneumatic devices, in addition to the filters, amplifiers, multiplexer and A/D converter. In considering whether a new type of sensor should be added to a pod or a cartridge, isolation requirements may be a factor, since each cartridge provides its own isolation.

DOCKING STATION

Figure 6:
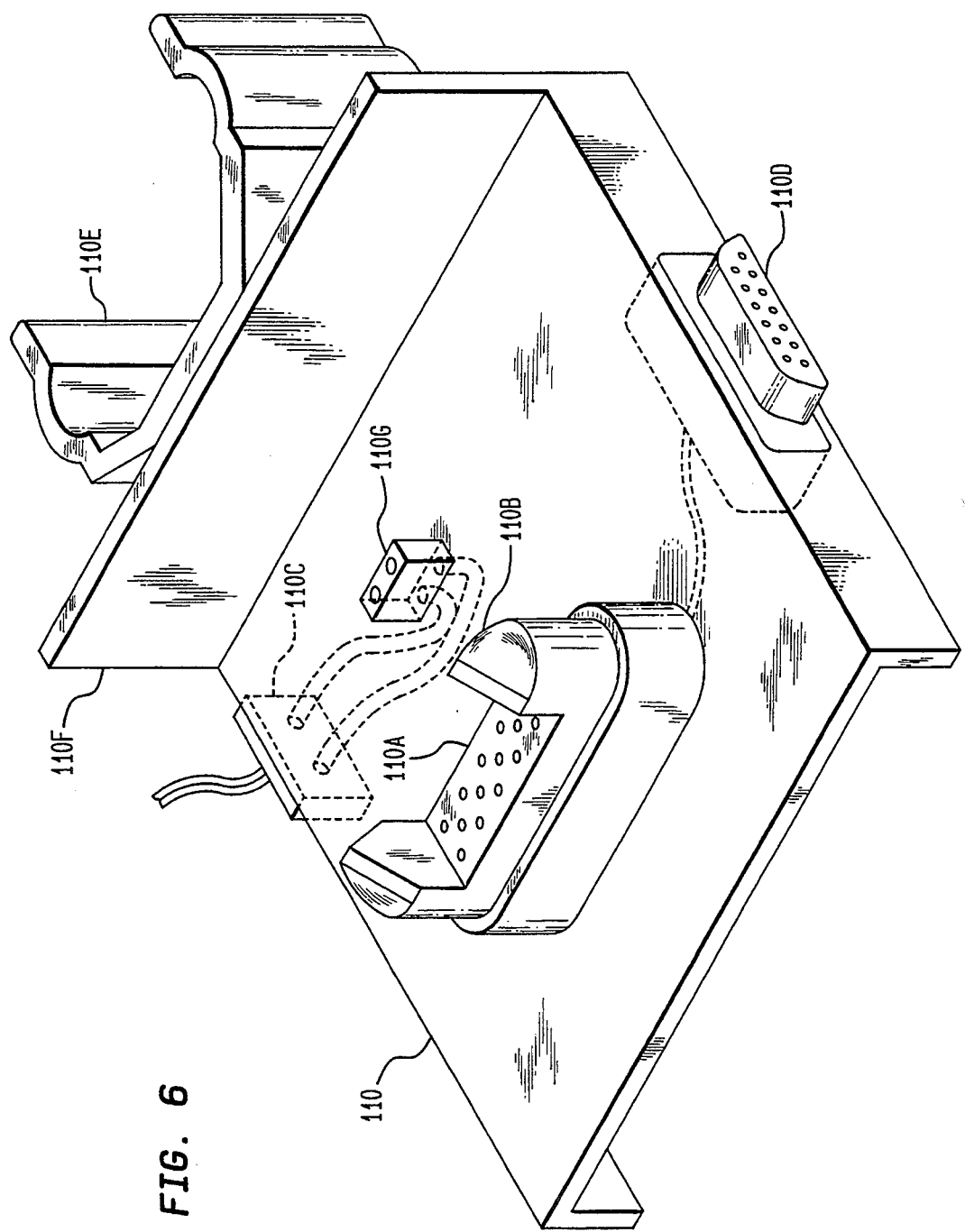

FIG. 6 shows docking station 110 to which portable monitor 102 may be attached. A connector 110a provides data communications couplings to the portable monitor. A guide 110b, which may be integral with connector 110a as shown in FIG. 6, facilitates proper positioning of monitor 102 on docking station 110, and assists in maintaining monitor 102 in position while monitor 102 is on docking station 110. A separate connector 110g provides power. Respective connectors 110c and 110d provide power and data communications links from portable monitor 102 to external power sources, devices and networks, when monitor 102 is on docking station 110. Connector 102d may be a conventional connector to interface directly to an Ethernet ™ LAN 118 (shown in FIG. 1A). Additionally, the data may be output to a remote display 120 or 122, or to an intelligent workstation, for display in VGA format.

An optional clamp 110e may be used to mount a docking station on an intravenous pole (not shown). Alternatively, clamp 110e may be omitted and backplate 110f may be fastened directly to a wall or bed.

Many variations of the docking station mechanical configuration are possible. For example, connector 110a and guide 110b may be separate from one another. There may be multiple connectors 110a and/or multiple connectors 110d. Additional mechanical fasteners may be added to improve the stability of the detachable mounting.

Connector 110d may alternatively connect to a smart wallbox 140, as indicated in FIG. 1a. The wallbox converts the twisted pair CSMA/CD signal from line 136 (shown in FIG. 1a) to 10 Mbits/second Thinnet, which uses the IEEE 802.3 Type 10-Base-2 standard. This connection provides a LAN connection between portable monitor 102 and remote stations which may be patient monitoring systems or computers. A separate connection 138 provides 1 Mbit/second communications with an input/output device LAN, which may include keyboards, pointing devices, voice input, bar code readers and label printers. Eight additional multi-vendor ports (MVP) 130 are provided. Four analog output ports provide waveform data for transmission to external devices (e.g., monitors, recorders). Wall box 140 assigns ID numbers to devices which connect to it. This allows the portable monitor to automatically identify any changes to the configuration devices connected to the wall box 140.

DATA TRANSFERS DURING CONNECTION

FIG. 7 is a flow diagram showing steps which are performed automatically to update the patient data in portable monitor 102 memory (the portable monitor data storing means), or the data in remote display 120 memory (assuming that remote display 120 has storage), so that both are kept current. At step 750, portable monitor 102 is inserted in docking station 110, and the connection to the remote display 120 is established. At step 752, memory in the remote display 120 is checked for data. If there are no data then patient physiological data stored in the portable monitor 102 is downloaded to remote display 120 memory at step 754. If there are data in remote display 120, at step 756, a determination is made whether the data in remote display 120 and the data in portable monitor 102 are associated with the same patient. A double comparison is made; both patient name and patient identification are compared. If either the name or the ID do not match, or if either the name or ID is blank, then the data in the portable monitor 102 and remote display 120 are considered to be associated with two different patients.

If the data are from two different patients, at step 758 remote display 120 will prompt the operator to choose either the data in remote display 120 or the data in portable monitor 102. Once the operator has selected one of the sets of data, at step 760 the data are copied from remote display 120 to the portable monitor 102 if remote display 120 is selected, or from portable monitor 102 to remote display 120 if portable monitor 102 is selected.

If it is determined at step 756 that the data in remote display 120 and portable monitor 102 are associated with the same patient, then at step 762, a determination is made whether the data in remote display 120 are newer than the data in portable monitor 102. If the portable monitor data are newer, then at step 764 the portable monitor data are copied to remote display 120. If the remote display data are newer, then at step 766, the remote display data are copied to portable monitor 102.

The same sequence of steps is performed when memory card 106 is inserted into monitor 102, except that monitor 102 exchanges data with memory card 106 instead of remote display 120. It is understood that replacing display 120 with memory card 106 in steps 750 through 766 above, the data in monitor 102 and memory card 106 are kept current.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

What is claimed is:

1. A continuous patient monitoring apparatus for normally continuously displaying, on a display device, medical data processed and collected from a patient using a plurality of sensors, the apparatus adapted for use in a system which includes a plurality of individual patient mounted sensors, the apparatus comprising:
   a docking station;
   at least one data acquisition module which is remote from and selectively communicating with the plurality of individual patient mounted sensors, the data acquisition module including:
      means for collecting patient data from the sensors, and
      means for generating conditioned data from the patient data; and
   a portable monitor, detachably coupled to the data acquisition module, which substantially continuously receives the conditioned data from the data acquisition module when coupled thereto and stores the conditioned data, the portable monitor being detachably coupled to the docking station.

2. Apparatus in accordance with claim 1, in which the portable monitor includes a display device, wherein conditioned data are displayed on the display device of the portable monitor.

3. Apparatus in accordance with claim 2, in which the portable monitor comprises:
   (a) means for receiving power from the docking station;
   (b) first transmitting means for transmitting the conditioned data to a remote display device by way of the docking station; and
   (c) second transmitting means for transmitting the conditioned data to the remote display device when the portable monitor is not coupled to the docking station, wherein the conditioned data are displayed on either one of the remote display device and the display device of the portable monitor.

4. Apparatus in accordance with claim 3, wherein the portable monitor includes:
   means for storing setup data; and
   means for displaying a waveform in accordance with the setup data on either one of the remote display device and the display device of the portable monitor.

5. Apparatus in accordance with claim 1, in which the data acquisition module is a data acquisition cartridge including:
   means for detachably mounting the data acquisition cartridge to the portable monitor, and
   means for electrically coupling the data acquisition cartridge to the portable monitor to transfer the conditioned data to the portable monitor.

6. Apparatus in accordance with claim 5, in which the portable monitor includes a case and the mounting means includes means for attaching the data acquisition cartridge to the case.

7. Apparatus in accordance with claim 5, in which the data acquisition cartridge includes:
   means for receiving a plurality of patient physiological parameter data from the plurality of sensors; and
   means for generating from the plurality of patient physiological parameter data a combined signal which is transferred to the portable monitor.

8. Apparatus in accordance with claim 7, wherein the generating means include:
   means for producing a time division multiplexed signal from the patient data; and
   means for converting the multiplexed signal to a digital signal, wherein the combined signal is a time division multiplexed digital data signal.

9. Apparatus in accordance with claim 5, in which the data acquisition cartridge includes means for receiving patient blood pressure data from a non-invasive blood pressure sensor.

10. Apparatus in accordance with claim 5, in which the data acquisition cartridge includes means for receiving patient inhaled and exhaled carbon dioxide partial pressure data from a selected one of the plurality of sensors.

11. Apparatus in accordance with claim 1, in which the portable monitor includes a case, the apparatus further comprising means for detachably mounting a hardcopy output device to the case.

12. Apparatus in accordance with claim 11, in which the mounting means comprises:
   means for mounting the hardcopy output device to the case; and
   means for electrically coupling the hardcopy output device to the portable monitor to transfer the digital data to the hardcopy output device.

13. Apparatus in accordance with claim 1, in which the portable monitor includes a case, the apparatus further comprising means for detachably connecting a battery pack to the case, the connecting means comprising:
   means for mounting the battery pack to the case; and
   means for receiving power from the battery pack.

14. Apparatus in accordance with claim 1, in which the data acquisition module is an independently positionable, self-contained data acquisition pod.

15. Apparatus in accordance with claim 14, in which the data acquisition pod comprises:
   means for receiving a plurality of patient physiological parameter data from the plurality of sensors; and
   means for generating from the plurality of physiological parameter data a combined signal which is transferred to the portable monitor.

16. Apparatus in accordance with claim 15, wherein the generating means include:
   means for producing a time division multiplexed signal from the patient data; and
   means for converting the multiplexed signal to a digital signal, wherein the combined signal is a time division multiplexed digital data signal.

17. Apparatus in accordance with claim 14, in which the data acquisition pod includes means for receiving patient electrocardiogram data, blood oxygen saturation data and either one of temperature data and cardiac output data.

18. Apparatus in accordance with claim 17, in which the data acquisition pod further includes means for receiving data representative of patient electroencephalogram signals.

19. Apparatus in accordance with claim 18, in which the data acquisition pod further includes means for receiving at least one of the group consisting of blood oxygen partial pressure data and blood carbon dioxide partial pressure data.

20. Apparatus in accordance with claim 14, in which the data acquisition pod includes means for receiving data representative of patient blood pressure data.

21. Apparatus in accordance with claim 20, in which the data acquisition pod includes means for receiving patient temperature data.

22. Apparatus in accordance with claim 1, in which the portable monitor includes:
   a non-volatile memory for storing a first set of instructions which are executable by the portable monitor;
   means for reading a second set of instructions from a random access memory card; and
   means for replacing the first set of instructions in the non-volatile memory with the second set of instructions.

23. Apparatus in accordance with claim 1, in which the portable monitor includes:
   means for storing patient data in a random access memory card, wherein the patient data include patient identification information, patient physiological trends and alarm limits; and
   means for reading the patient data from the random access memory card.

24. Apparatus in accordance with claim 1, wherein the portable monitor includes:

means for transferring data to a remote display device which has a remote display memory for storing the patient data;

means for receiving data from the remote display device;

a portable monitor memory for storing the patient data;

means for determining whether the data stored in the portable monitor memory are older than the data stored in the remote display memory;

replacing means for replacing the data stored in the portable monitor memory with the data stored in the remote display memory if the data stored in the portable monitor memory are older than the data stored in the remote display memory; and means for transmitting the data stored in the portable monitor memory to the remote display memory if the data stored in the remote display memory are older than the data stored in the portable monitor memory.

25. A continuous patient monitoring apparatus for normally continuously displaying, on a display device, medical data collected from a patient using a plurality of sensors, the apparatus adapted for use in a system which includes a remote display device and a plurality of remote and individual patient mounted sensors, the apparatus comprising:

a docking station which provides electrical power and a path for transmitting data;

a plurality of data acquisition modules coupled to the plurality of sensors, the data acquisition modules including means for collecting patient data from the sensors and means for providing the collected patient data at an output port, the plurality of data acquisition modules including at least one selectably positionable data acquisition pod and at least one data acquisition cartridge; and a portable monitor, detachably coupled to the plurality of data acquisition modules, for receiving the patient data provided at the output port of the data acquisition modules and for storing the data, the portable monitor being detachably coupled to the docking station, the portable monitor comprising:

(a) means for receiving power from the docking station, and (b) means for substantially continuously transmitting the patient data to the remote display device by way of the docking station when the portable monitor is coupled to the docking station; and means for detachably mounting the data acquisition cartridge to the portable monitor.

26. Apparatus in accordance with claim 25, in which each of the plurality of data acquisition modules comprises:

means for receiving signals representing analog patient physiological conditions from the plurality of sensors;

means for combining the plurality of analog patient physiological condition signals to form a combined signal; and means for receiving the combined signal and for generating therefrom a time division multiplexed digital data signal.

* * * * *